(12) United States Patent
Weigl et al.

(10) Patent No.: US 9,797,345 B2
(45) Date of Patent: Oct. 24, 2017

(54) METHOD FOR MONITORING FOR A RUPTURE IN A FUEL VAPOR CONTAINER

(71) Applicant: CONTINENTAL AUTOMOTIVE GMBH, Hannover (DE)

(72) Inventors: Manfred Weigl, Sinzing (DE); Philippe Grass, Regensburg (DE)

(73) Assignee: Continental Automotive GmbH, Hannover (DE)

(*) Notice: Subject to any disclaimer, the term of this patent is extended or adjusted under 35 U.S.C. 154(b) by 72 days.

(21) Appl. No.: 14/892,877

(22) PCT Filed: Apr. 23, 2014

(86) PCT No.: PCT/EP2014/058207
§ 371 (c)(1),
(2) Date: Nov. 20, 2015

(87) PCT Pub. No.: WO2014/187635
PCT Pub. Date: Nov. 27, 2014

(65) Prior Publication Data
US 2016/0084207 A1 Mar. 24, 2016

(30) Foreign Application Priority Data
May 24, 2013 (DE) .................. 10 2013 209 715

(51) Int. Cl.
*F02M 25/08* (2006.01)
*G01M 3/32* (2006.01)
(Continued)

(52) U.S. Cl.
CPC .... *F02M 25/0809* (2013.01); *F02M 25/0818* (2013.01); *G01M 3/3209* (2013.01); *G01N 25/18* (2013.01); *B60K 2015/03514* (2013.01); *F02M 25/089* (2013.01); *F02M 25/0836* (2013.01); *F02M 25/0854* (2013.01); *F02M 25/0872* (2013.01)

(58) Field of Classification Search
CPC .......... F02M 25/0809; F02M 25/0818; G01M 3/3209; G01N 25/18
See application file for complete search history.

(56) References Cited

U.S. PATENT DOCUMENTS 8,573,187 B2    11/2013  Knittel et al.
2004/0060343 A1  4/2004  Amano et al.
(Continued)

FOREIGN PATENT DOCUMENTS

DE    10 2008 031 649       1/2010
DE    10 2008 045 322 A1    3/2010
(Continued)

*Primary Examiner* — Hezron E Williams
*Assistant Examiner* — David Z Huang
(74) *Attorney, Agent, or Firm* — Cozen O'Connor

(57) ABSTRACT

A method for monitoring for a rupture in a storage element of a fuel tank system having a fuel tank includes: detecting, by a mass flow sensor, thermal conductivity of an unmoved air mass in a first line of the fuel tank system; and identifying a rupture in the storage element if the detecting by the mass flow sensor detects a change in the thermal conductivity of the unmoved air mass in the first line when a second valve is in a closed state and/or when an air pump is at a standstill.

6 Claims, 2 Drawing Sheets

(51) Int. Cl.
*G01N 25/18* (2006.01)
*B60K 15/035* (2006.01)

(56) References Cited

U.S. PATENT DOCUMENTS

2005/0022594 A1* 2/2005 Padmanabhan ......... G01F 1/684
 73/204.26
2005/0229688 A1 10/2005 Miyahara et al.

FOREIGN PATENT DOCUMENTS

| | | |
|---|---|---|
| DE | 10 2010 054 668 | 6/2012 |
| KR | 20120024294 | 3/2012 |

* cited by examiner

METHOD FOR MONITORING FOR A RUPTURE IN A FUEL VAPOR CONTAINER

CROSS-REFERENCE TO RELATED APPLICATIONS

This is a U.S. national stage of application No. PCT/EP2014/058207, filed on 23 Apr. 2014, which claims priority to the German Application No. DE 10 2013 209 715.8 filed 24 May 2013, the content of both incorporated herein by reference.

BACKGROUND OF THE INVENTION

1. Field of the Invention

The invention relates to a method for monitoring for a rupture in (i.e., a breakthrough through) a storage element of a fuel tank system.

2. Related Art

Numerous measures have been introduced in recent decades for reducing the pollutant emissions of motor vehicles. One such measure consists in using a fuel tank system in which a fuel tank is connected to a storage element for the temporary storage of hydrocarbons. During the refueling of motor vehicles, hydrocarbons are outgassed from the fuel, wherein it is sought to prevent the hydrocarbons from passing into the atmosphere. Also, in the presence of high temperatures or when driving over uneven surfaces, increased outgassing of hydrocarbons from the fuel occurs, wherein it must be ensured, in an effective manner, that the hydrocarbons do not escape into the atmosphere. In particular, in the case of hybrid vehicles, in which the internal combustion engine is entirely shut down over long traveling distances, it is necessary for outgassed hydrocarbons to be temporarily stored in an effective manner in order to be burned at a later point in time upon a restart of the internal combustion engine. For this purpose, fuel tank systems have become established that are composed of a fuel tank and a storage element for the temporary storage of hydrocarbons, wherein the fuel tank and the storage element are connected to one another such that the hydrocarbons outgassed from a fuel situated in the fuel tank are stored in the storage element, wherein the storage element is connected to a first line through which fresh air can be delivered to the storage element, and the storage element is connected to a second line connecting the storage element to an intake line and through which fresh air enriched with hydrocarbons can be delivered from the storage element to the intake line. In this way, the storage element can be cyclically purged with fresh air, and the stored hydrocarbons can be supplied to an intake line connecting the internal combustion engine to the air filter and supplying air for combustion to the internal combustion engine. It is thus possible for the hydrocarbons outgassed from the fuel tank to be burned in the internal combustion engine, reliably preventing escape of the hydrocarbons into the atmosphere.

An example of a fuel tank system according to the prior art can be found in the PCT application with the file reference PCT/KR2011/006516. The storage element however has only a limited storage capacity for the hydrocarbons outgassed from the fuel, which is a problem in particular in the case of hybrid vehicles, because the internal combustion engine of a hybrid vehicle is at a standstill over long distances and periods of time. When the capacity limit of the storage element has been reached, there is the risk, in the event of a further follow-up flow of hydrocarbons from the fuel tank into the storage element, of a so-called breakthrough of the hydrocarbons through the storage element. In the event of a breakthrough of this type through the storage element, no further hydrocarbons can be captured by the storage element, and the hydrocarbons seek a path through the storage element into the surroundings of the tank system and thus into the atmosphere. Therefore, it is necessary over the entire service life of the motor vehicle to reliably identify a rupture in (i.e., breakthrough through) the storage element, in order for the rupture in the storage element to be prevented "on board", that is to say during the operation of the motor vehicle, for example by virtue of a purging process of the storage element being initiated, wherein the outgassed hydrocarbons are depleted by being burned in the internal combustion engine.

SUMMARY OF THE INVENTION

It is therefore an object of the present invention to specify a reliable and inexpensive method with which a rupture in a storage element during the operation of the motor vehicle can be identified.

If a rupture in the storage element is identified if the mass flow sensor detects a change in the thermal conductivity of the unmoved air mass in the first line when the first valve is in a closed state and/or when the second valve is in a closed state and/or when the air pump is at a standstill, it is possible for the already existing mass flow sensor to be used to identify a rupture in the storage element. The mass flow sensor in the fuel tank system is originally used for measuring the air mass delivered into the system during the purging process in order to obtain information regarding the air mass additionally introduced into the intake line and the amount of hydrocarbons conveyed to the intake line with the air mass. However, if no purging process is performed, because the storage element still has storage capacity, the air mass sensor has not been required in methods according to the prior art, because no air mass flow has been present for measurement. In the method according to the invention, the mass flow sensor is now provided with a new task for the time in which no purging process of the fuel tank system is performed. According to an aspect of the invention, in the time in which no purging process of the fuel tank system is performed, the mass flow sensor can be used as a sensor for monitoring for a rupture in the storage element. Specifically, if hydrocarbons break through the storage element into the first line, and no air mass flow is present in the first line, that is to say the system is not purged, the thermal conductivity of the air, which is enriched with hydrocarbons after the rupture in the storage element, changes. This change in the thermal conductivity of the air in the first line can be detected by the mass flow sensor, whereby a rupture in the storage element can be reliably identified.

In one refinement, the air pump is in the form of a radial pump. A radial pump has an easily reproducible relationship between the pressure it generates and the rotational speed at which it is driven, or the power that it consumes, if the physical parameters, for example the temperature, of the delivered air are known. If the radial pump is, however, at a standstill, it is possible, after a rupture in the storage element, for hydrocarbons to penetrate as far as the mass flow sensor, whereby the mass flow sensor can, even upstream of the air pump, be utilized for identifying a rupture in the storage element.

In one refinement of the invention, the mass flow sensor is in the form of a sensor that operates on the basis of the thermal principle. Such mass flow sensors are robust and durable components, which can furthermore be produced in highly economical fashion in high unit quantities. It is advantageous for the mass flow sensor to be integrated in the housing of the air pump.

If a first valve is additionally arranged in the first line, it is possible, in the event of a rupture in the storage element, for an escape of the hydrocarbons into the atmosphere to be immediately prevented by way of the closure of the first valve.

In one advantageous refinement of the invention, a rupture in the storage element is identified if the mass flow sensor detects a change in the thermal conductivity of the air in the first line when the first valve is in a closed state. If the first valve is closed already after the completion of a purging process, an escape of the hydrocarbons through the first line into the atmosphere is not possible even in the event of a rupture in the storage element. The mass flow sensor nevertheless identifies the rupture in the storage element, and suitable measures for evacuating the storage element can be initiated.

BRIEF DESCRIPTION OF THE DRAWINGS

An advantageous embodiment of the invention will be described on the basis of the figures, in which.

DETAILED DESCRIPTION OF THE PRESENTLY PREFERRED EMBODIMENTS

Figure 1:
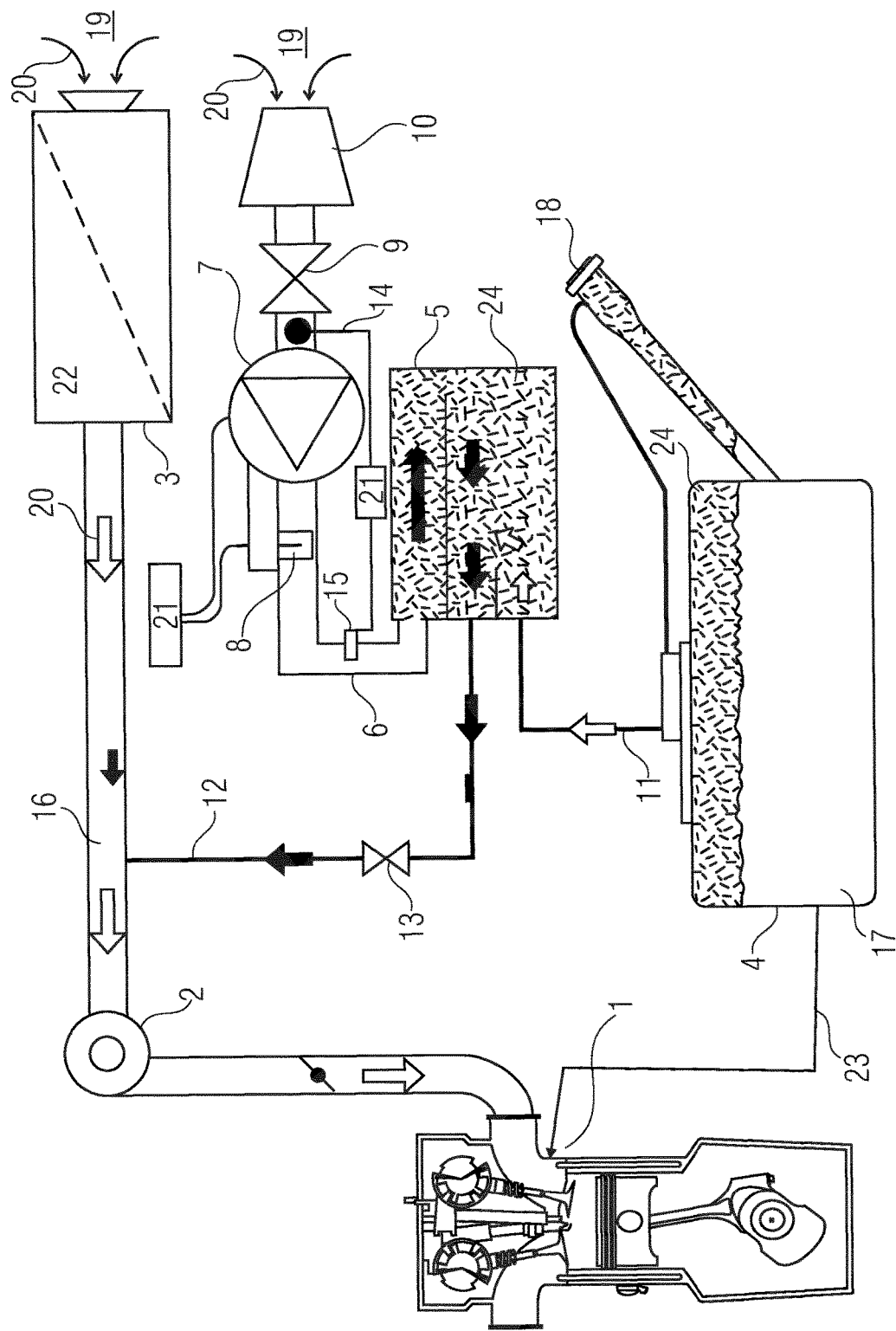
FIG. 1 shows an internal combustion engine having a fuel tank system according to the invention.

FIG. 1 shows an internal combustion engine 1. The internal combustion engine 1 is supplied with fresh air 20 via an intake line 16. Proceeding from the fresh-air side 19, fresh air 20 is conducted into the intake line 16 via an air filter 22, is possibly compressed by way of an exhaust-gas turbocharger 2 or a supercharger, and is then supplied to the combustion chambers of the internal combustion engine 1. Furthermore, fuel 17 is supplied to the internal combustion engine 1 from the fuel tank 4 via a fuel line 23.

FIG. 1 furthermore shows the fuel tank system with a fuel tank 4 and a storage element 5 for the temporary storage of hydrocarbons 24. The fuel tank 4 and the storage element 5 are connected to one another such that the hydrocarbons 24 outgassed from a fuel 17 situated in the fuel tank 4 can be stored in the storage element 5. The storage element 5 may, for example, be in the form of an activated carbon store. An activated carbon store is a closed canister in which carbon is arranged such that the hydrocarbons 24 for storage accumulate on the carbon. The storage element 5 however has a limited storage capacity, and therefore the storage element 5 must be regularly evacuated by virtue of fresh air 20 being drawn in, for example via a dust filter 10, and being forced into the storage element 5 via a first line 6 by way of an air pump 7. The fresh air 20 flows through the activated carbon in the storage element 5 and, in the process, absorbs hydrocarbons 24, whereafter the fresh air 20 enriched with the hydrocarbons 24 is delivered along a second line 12 to the intake air line 16. In the intake air line 16, the fresh air 20 enriched with the hydrocarbons 24 mixes with the fresh air 20 that is drawn in via the air filter 22. It is thus possible for the hydrocarbons 24 to be supplied to the internal combustion engine 1, wherein the hydrocarbons 24 can be burned in the combustion chambers.

The fuel tank system illustrated in FIG. 1 has a first valve 9 arranged in the first line 6 upstream of the storage element 5 as viewed in the direction of the fresh-air flow. An air pump 7 is likewise arranged in the first line 6, between the first valve 9 and the storage element 5. The first line 6 issues into the storage element 5. A second valve 13 is arranged in a second line 12 between the storage element 5 and the intake line 16. Furthermore, a temperature sensor 14 may be arranged in the first line 6, which temperature sensor detects the temperature of the fresh air 20 delivered by the air pump 7.

Furthermore, a mass flow sensor 8 is arranged in the first line 6, preferably in the housing of the air pump 7. This mass flow sensor 8 may, for example, operate on the basis of the thermal (i.e., calorimetric) principle. An example of a mass flow sensor 8 that operates on the basis of the thermal (i.e., calorimetric) principle is a hot-wire anemometer. Within the mass flow sensor 8 there are situated at least two wires, for example platinum wires, or film resistors, which are heated by electrical current. One wire or resistor is cooled directly by the air flowing past, and the other is situated in a position shielded from the flowing air. The flow of electrical current causes both resistor elements to be heated, wherein the air flowing past cools the non-shielded heating element more intensely than that which is shielded from the air. The heating element therefore heats up to a greater degree, and the resistance thereof thus increases. From the resistance values of the two heating elements, and the difference thereof, it is possible, by a characteristic map, to derive the mass flow of the fresh air in the first line 6 and the presence of hydrocarbons in the air, that is to say also a breakthrough through the storage element.

Figure 2:
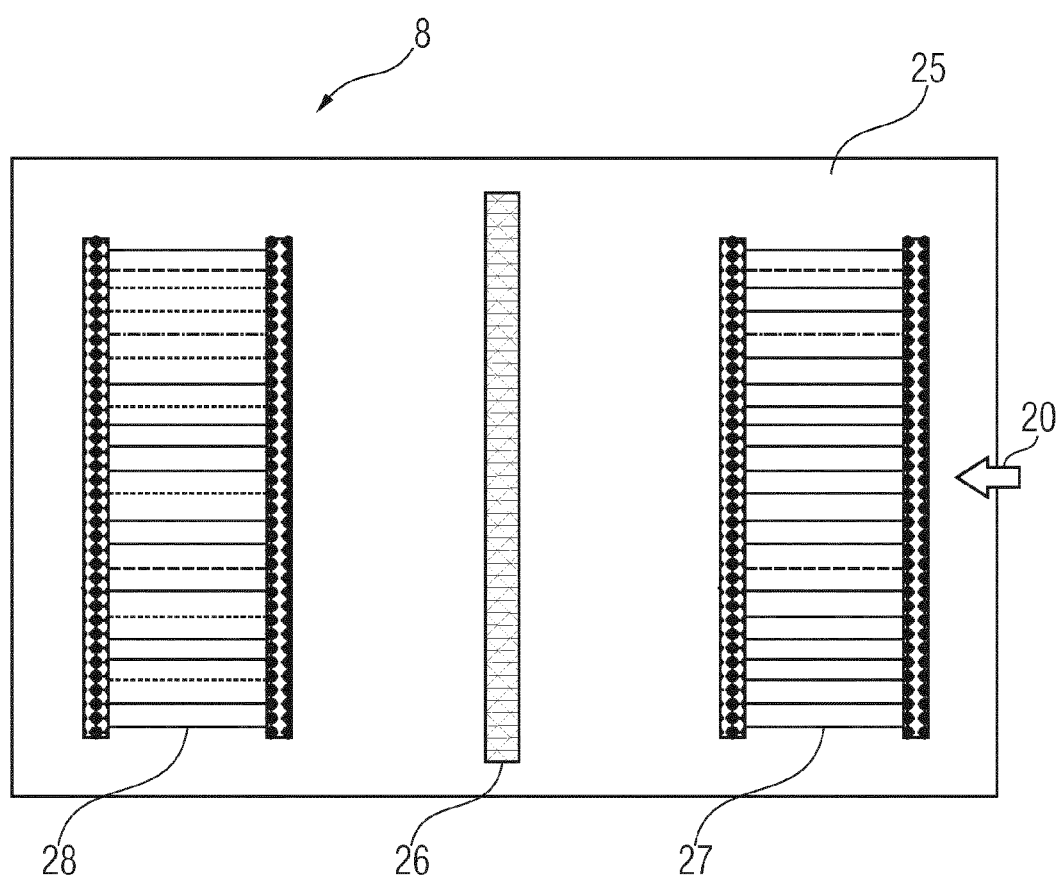
FIG. 2 shows a further example of a mass flow sensor.

A further example of a mass flow sensor 8 that operates on the basis of the thermal principle is illustrated in FIG. 2. A heating element 26, preferably an electrical resistance heating element, is applied to a substrate element 25, which may, for example, be composed of silicon nitrate (glass). A first temperature measurement element 27 and a second temperature measurement element 28 are arranged on the substrate element 25 upstream and downstream of the heating element 26 as viewed in the direction of the air flow 20. The first and the second temperature measurement element 27, 28 may be in the form of thermopiles.

A method according to the invention for monitoring for a breakthrough through a storage element 5 of a fuel tank system can be performed with the fuel tank system illustrated in FIG. 1. In the method according to the invention, firstly the first valve 9 and/or the second valve 13 are/is closed, and/or the air pump 7 is brought to a standstill. By these measures, it is ensured that the air in the first line 6 is not moving, whereby the mass flow sensor cannot detect an air mass flow. In the known methods for identifying a rupture in the storage element 5, the mass flow sensor 8 would be useless in this situation. According to the invention, however, the mass flow sensor 8 is now utilized to monitor the loading of the storage element 5 such that a breakthrough of hydrocarbons, that is to say an overflow of the storage element 5, is reliably identified. This is realized in that the mass flow sensor 8 detects a change in thermal conductivity of the unmoved air mass in the first line 6. In this context, the expression "unmoved air mass" means that no air mass flow is present in the first line 6. It is self-evidently the case that the individual particles in the air in the first line move, but the movement is disordered and, averaged over all of the moving air particles, there is no resultant movement of the air mass as a whole when the first valve 9 and/or the second valve 13 is in a closed state and/or the air pump 7 has been brought to a standstill. Thus, only Brownian molecular motion occurs in the unmoved or static air mass.

Now, in the case of a static air mass, should a change in the thermal conductivity of the air in the first line 6 be detected by the mass flow sensor 8, this can only have occurred owing to a breakthrough of the hydrocarbons through the storage element 5. Thus, the breakthrough of the hydrocarbons through the storage element 5 can be reliably detected, and measures can be implemented which prevent an escape of the hydrocarbons into the surroundings of the fuel tank system. The immediate initiation of purging of the storage element 5 with fresh air is a suitable measure which can prevent the escape of the hydrocarbons. In the case of hybrid vehicles, it may be necessary to start the internal combustion engine in order that the hydrocarbons purged from the storage element 5 can also be burned. All of the measures can be initiated by a control unit 21, wherein the control unit 21 is also configured to process the data detected by the mass flow sensor 8 and to detect information regarding the position of the first valve 9 and of the second valve 13 and the operating state of the air pump 7.

Thus, while there have been shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A method for monitoring for a rupture in a storage element (5) of a fuel tank system, the fuel tank system having a fuel tank (4) and the storage element (5) being configured to temporarily store hydrocarbons, the fuel tank (4) and the storage element (5) being connected to one another such that hydrocarbons outgassed from fuel situated in the fuel tank (4) are stored in the storage element (5), the storage element (5) being connected to a first line (6) through which fresh air is deliverable to the storage element (5), and the storage element (5) being connected to a second line (12) connecting the storage element (5) to an intake line (16) and through which fresh air enriched with hydrocarbons is deliverable from the storage element (5) to the intake line (16), wherein a mass flow sensor (8) and an air pump (7) are arranged in the first line (6) upstream of the storage element (5) as viewed in the direction of the fresh air flow, and a second valve (13) is arranged in the second line (12) between the storage element (5) and the intake line (16), the method comprising:

detecting, by the mass flow sensor (8), thermal conductivity of an unmoved air mass in the first line (6); and identifying that a rupture has occurred in the storage element (5) if the detecting by the mass flow sensor (8) detects a change in the thermal conductivity of the unmoved air mass in the first line (6) in a case in which the second valve (13) is in a closed state and/or in a case in which the air pump (7) is at a standstill.

2. The method as claimed in claim 1, wherein the air pump (7) is a radial pump.

3. The method as claimed in claim 1, wherein the mass flow sensor (8) is a sensor that operates based on the calorimetric principle.

4. The method as claimed in claim 3, wherein the mass flow sensor (8) is integrated in the housing of the air pump (7).

5. The method as claimed in claim 4, wherein the fuel tank system further has a first valve arranged in the first line (6).

6. The method as claimed in claim 5, wherein a rupture in the storage element (5) is identified if the mass flow sensor (8) detects a change in the thermal conductivity of the air in the first line (6) when the first valve is in the closed state.

* * * * *